United States Patent
Pongó et al.

(10) Patent No.: US 7,307,168 B2
(45) Date of Patent: Dec. 11, 2007

(54) PROCESS FOR THE PREPARATION OF 3-{2-'4- (6-FLUORO-1,2-BENZISOXAZOL-3-YL)-1-PIPERIDINYLLETHYL}-6,7,8,9-TETRAHYDRO-2-METHYL-4H-PYRIDO '1,2-METHYL-4H-PYRIDO',2-A!PYRIMIDIN-4-ONE

(75) Inventors: László Pongó, Kerepes (HU); József Reiter, Budapest (HU); Gyula Simig, Hudapest (HU); Gábor Berecz, Budapest (HU); György Clementis, Budapest (HU); Péter Slégel, Budapest (HU); János Szulágyi, Budapest (HU); László Koncz, Mogyoród (HU); Györgyi Vereczkeyné Donáth, Budapest (HU); Kálmán Nagy, Budapest (HU); Gyuláné Körtvélyessy, Budapest (HU)

(73) Assignee: EGIS Gyógyszergyár Rt., Budapest (HU)

( * ) Notice: Subject to any disclaimer, the term of this patent is extended or adjusted under 35 U.S.C. 154(b) by 509 days.

(21) Appl. No.: 10/495,362

(22) PCT Filed: Nov. 13, 2002

(86) PCT No.: PCT/HU02/00120

§ 371 (c)(1),
(2), (4) Date: Aug. 20, 2004

(87) PCT Pub. No.: WO03/042212

PCT Pub. Date: May 22, 2003

(65) Prior Publication Data

US 2005/0004141 A1 Jan. 6, 2005

(30) Foreign Application Priority Data

Nov. 13, 2001 (HU) .................................. 0104873

(51) Int. Cl.
*C07D 239/70* (2006.01)

(52) U.S. Cl. ...................... 544/282; 544/224; 544/242; 544/245; 544/253

(58) Field of Classification Search ................ 544/224, 544/242, 245, 253, 282
See application file for complete search history.

(56) References Cited

U.S. PATENT DOCUMENTS

| | | | | |
|---|---|---|---|---|
| 5,482,943 A | * | 1/1996 | Kennis et al. | ......... 514/259.41 |
| 5,658,916 A | * | 8/1997 | Caldero Ges et al. | .. 514/259.41 |
| 6,897,308 B1 | * | 5/2005 | Venkatasubramanian et al. | ..................... 544/282 |

FOREIGN PATENT DOCUMENTS

EP 0 196 132 A 10/1986

OTHER PUBLICATIONS

Marquillas et al (1994): STN International HCAPLUS database, Columbus (Ohio), accession No. 1994:655824.*

* cited by examiner

*Primary Examiner*—Golam M. M. Shameem
(74) *Attorney, Agent, or Firm*—Birch, Stewart, Kolasch & Birch, LLP

(57) ABSTRACT

The invention relates to a process for the preparation of 3-{2-[4-(6-fluoro-1,2-benzisoxazol-3-yl)-1-piperidinyl] ethyl}-6,7,8,9-tetrahydro-2-methyl-4H-pyrido[1,2-a]pyrimidin-4-one of the Formula (I), and pharmaceutically acceptable acid addition salts thereof by subjecting the oxime of the Formula (II), to ring-closure in the presence of an alkali hydroxide, alkali carbonate or alkali-$C_{1-4}$ alkoxide in an inert organic solvent, converting the base of the Formula I thus obtained into an acid addition salt or setting free the base of the Formula I from an acid addition salt thereof which comprises reacting a halogen derivative of the general Formula (XIV), (wherein Hal is halogen) with piperidine oxime derivative of the Formula (V), or an acid addition salt thereof in the presence of a base, and using by the ring-closure of the oxime of the Formula II formed a $C_{1-4}$-alkanol as inert solvent. The process of the present invention enables the economical preparation of a product having a purity suitable for pharmaceutical purposes.

7 Claims, 4 Drawing Sheets

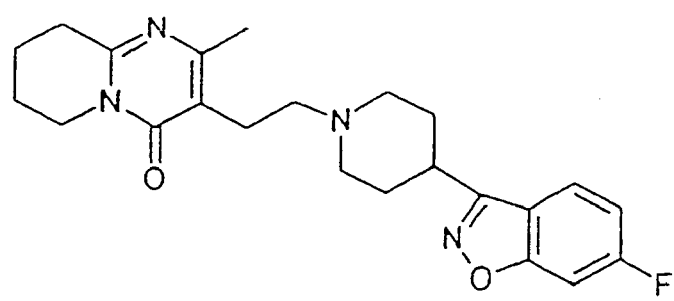
I
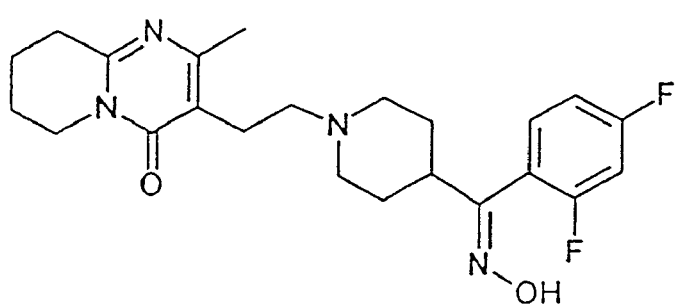
II
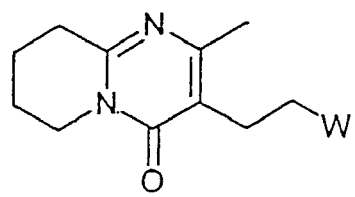
III
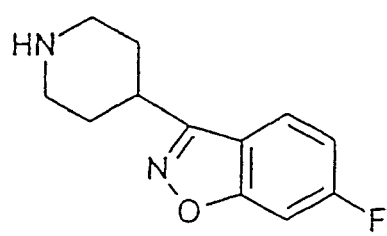
IV

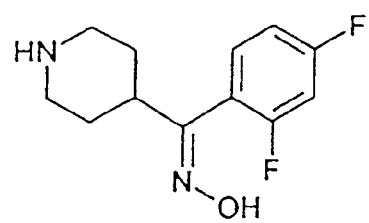
V
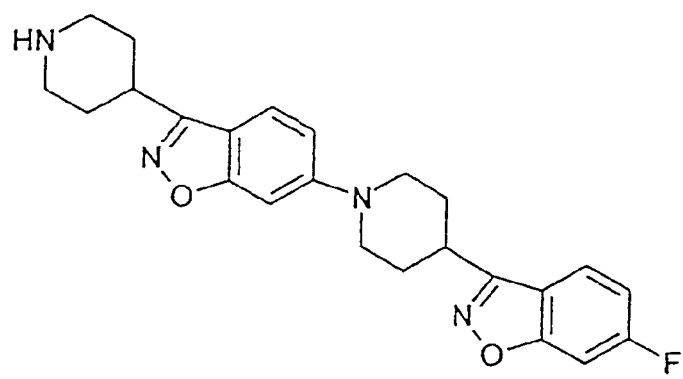
VI
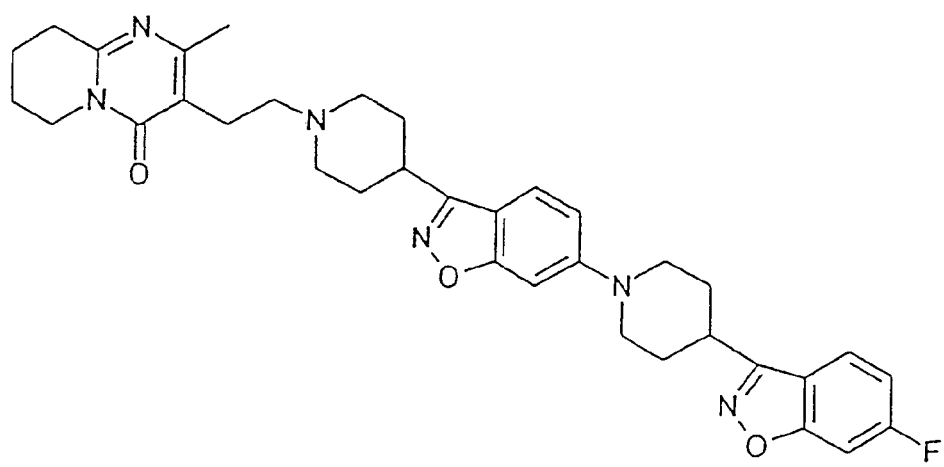
VII

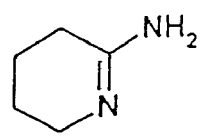
VIII
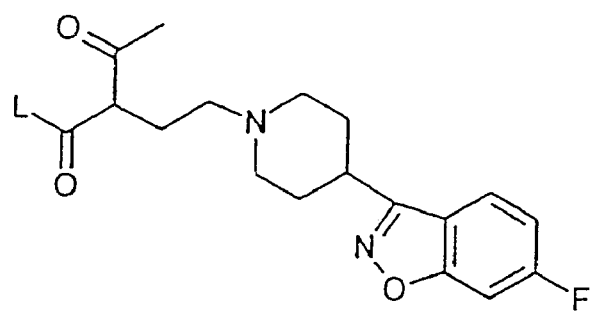
IX
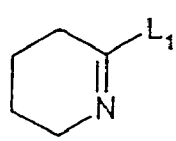
X
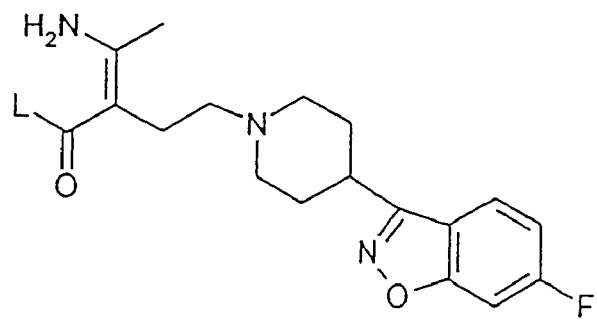
XI

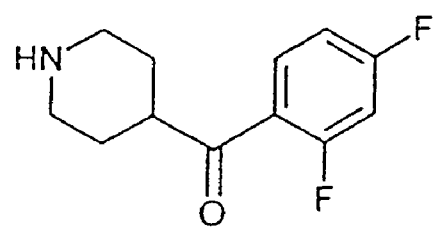
XII
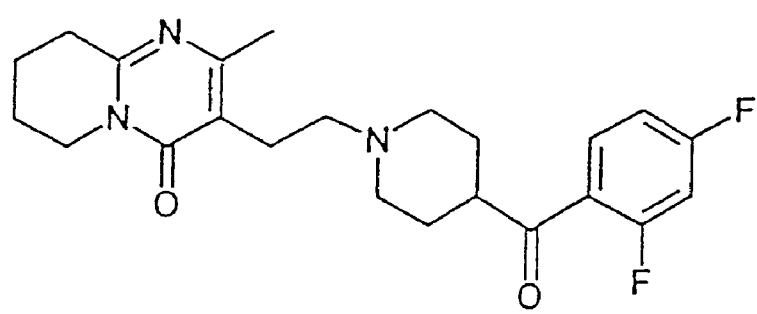
XIII
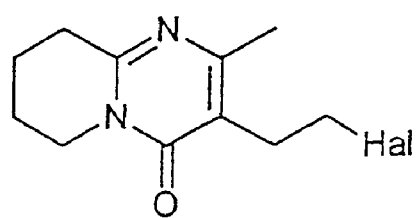
XIV

PROCESS FOR THE PREPARATION OF 3-{2-'4- (6-FLUORO-1,2-BENZISOXAZOL-3-YL)-1-PIPERIDINYLLETHYL}-6,7,8,9-TETRAHYDRO-2-METHYL-4H-PYRIDO '1,2-METHYL-4H-PYRIDO',2-A!PYRIMIDIN-4-ONE

TECHNICAL FIELD OF THE INVENTION

The invention relates to the preparation of 3-{2-[4-(6-fluoro-1,2-benzisoxazol-3-yl)-1-piperidinyl]ethyl}-6,7,8,9-tetrahydro-2-methyl-4H-pyrido[1,2-a]pyrimidin-4-one.

The compound 3-{2-[4-(6-fluoro-1,2-benzisoxazol-3-yl)-1-piperidinyl]ethyl}-6,7,8,9-tetrahydro-2-methyl-4H-pyrido[1,2-a]pyrimidin-4-one of the Formula

I

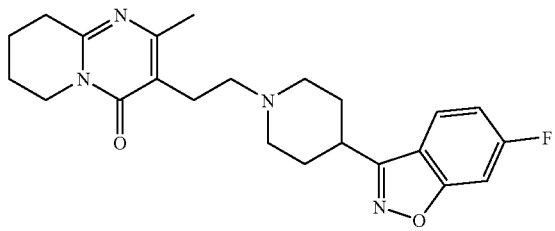

is a well-known antipsychotic agent having the INN (International Non-Proprietary Name) risperidone which can be used for the treatment of diseases related to serotonin release.

TECHNICAL BACKGROUND OF THE INVENTION

Several processes for the preparation of risperidone of the Formula I are disclosed in HU-P 195,793 and the corresponding EP-P 196,132. According to one of said processes a reactive derivative of the general Formula

III

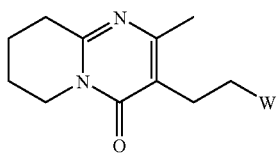

(wherein W is a reactive group e.g. halogen or an O-sulfonic acid ester group) is reacted in an inert solvent with a benzisoxazol derivative of the Formula

IV

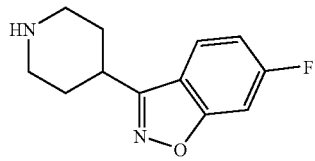

The disadvantage of said process is that the benzisoxazol derivative of the Formula IV is prepared by boiling the corresponding piperidine oxime derivative of the Formula

V

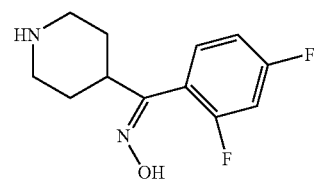

in a strongly alkaline medium and in the course of this reaction not only the desired fluorine atom in the ortho-position reacts but—according to our experiments—the fluorine atom in the para-position takes also part in the reaction at a rate of about 5%, to yield the dimer of the Formula

VI

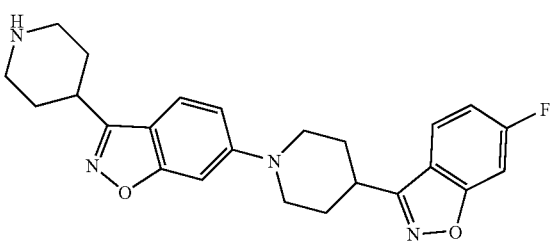

As shown in comparative Example 1 said dimer of the Formula VI contaminates the desired benzisoxazol derivative of the Formula IV. The dimer of the Formula VI is significantly less soluble than the benzisoxazol of the Formula IV and therefore practically it cannot be removed by recrystallization. Consequently, on converting the benzisoxazol derivative of the Formula IV contaminated with the dimer of the Formula VI to risperidone, said end-product contains about 3% of the impurity dimer of the Formula

VII

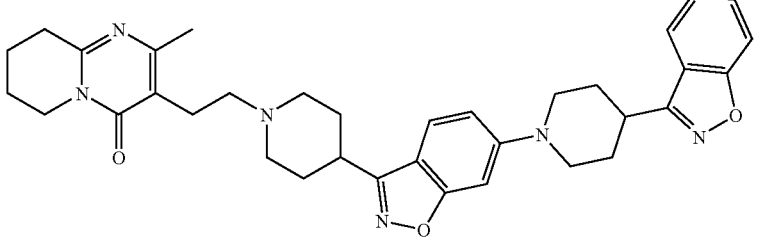

Since the dimer of the Formula VII is much less soluble than risperidone, it is practically impossible to remove the dimer of the Formula VII from risperidone. This is clearly shown in comparative Example 2.

According to another known process risperidone is prepared by reacting the amine of the Formula

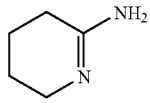
VIII with a diketone of the general Formula

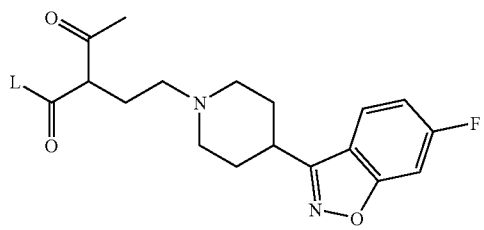
IX (wherein L is a leaving group). However, the preparation of the diketone of the Formula IX is neither described in the prior art citation nor is it exemplified and therefore this process is but of theoretical importance.

According to a further known process a compound of the general Formula

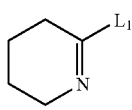
X (wherein $L_1$ is a leaving group) is reacted with a piperidine derivative of the general Formula

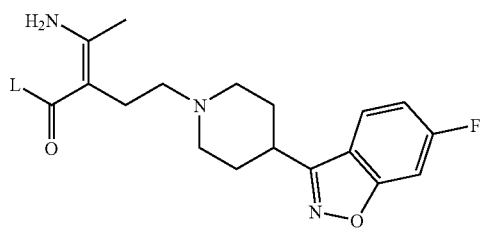
XI (wherein L is a leaving group). The prior art lacks an enabling disclosure and for this reason the skilled art worker is not in the position to carry out said process.

ES-P 2,050,069 aims to overcome the disadvantages of the known procedures. According to said Spanish patent a reactive derivative of the general Formula III is reacted with the ketone of the Formula

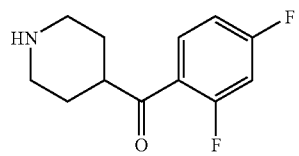
XII whereupon the piperidone derivative of the Formula

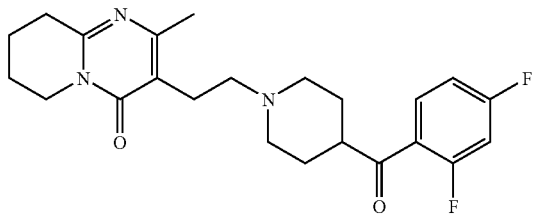
XIII formed is reacted with hydroxylamine and finally the oxime of the Formula

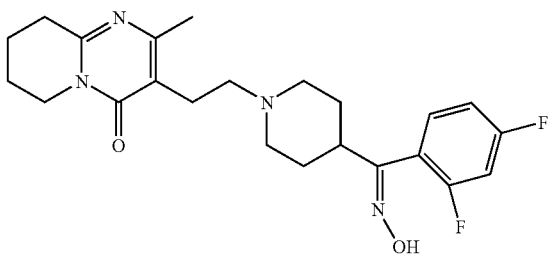
II thus obtained is subjected to cyclization in an inert solvent in the presence of a base. Cyclization which leads to risperidone is carried out either in water in the presence of an alkali hydroxide, alkali carbonate or alkali hydrogencarbonate, or is performed in tetrahydrofuran or dioxan in the presence of an alkali hydride or alkali alkoxide. Ring-closure is preferably carried out in aqueous medium, advantageously at the boiling point of the reaction mixture.

The advantage of this process is that the formation of the dimer of the Formula VII is eliminated. However, this process is accompanied by a very serious draw-back because the piperidone derivative of the Formula XIII formed in the synthesis can be purified only in a very complicated manner either by means of chromatography or via the poorly crystallizable hydrochloride. This has the consequence that the piperidone derivative is obtained only in relatively low yields. According to ES-P 2,050,069 the yield is only 63.1%. Moreover, we failed to reproduce the process with such yields because according to our experiments the yield of the hydrochloride of the piperidone derivative of the Formula XIII is below 60%. According to ES-P 2,050,069 the conversion of the piperidone derivative of the Formula XIII into the corresponding oxime of the Formula II is carried out with a yield of 76.2%. We have succeeded in reproducing the process according to ES-P 2,050,069 only with a yield of about 63%. According to ES-P 2,050,069 the yield of the cyclization of the oxime of the Formula II to risperidone is 79-85%, but we could reproduce only a yield of about 75%. Thus the process disclosed in the Spanish patent is not economical either. The aforesaid is illustrated by comparative Example 3.

SUMMARY OF THE INVENTION

It is the object of the present invention to elaborate an economical process for the preparation of risperidone.

The above object is solved by the present invention.

According to the present invention there is provided a process for the preparation of 3-{2-[4-(6-fluoro-1,2-benzisoxazol-3-yl)-1-piperidinyl]ethyl}-6,7,8,9-tetrahydro-2-methyl-4H-pyrido[1,2-a]pyrimidin-4-one of the Formula I and pharmaceutically acceptable acid addition salts thereof by subjecting the oxime of the Formula II to ring-closure in the presence of an alkali hydroxide, alkali carbonate or alkali-$C_{1-4}$-alkoxide in a $C_{1-4}$-alkanol as an inert organic solvent, converting the base of the Formula I thus obtained into an acid addition salt or setting free the base of the Formula I from an acid addition salt thereof which comprises reacting a halogen derivative of the general Formula

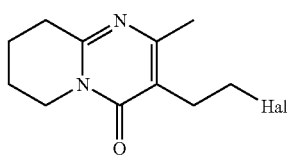

XIV (wherein Hal is halogen) with the piperidine oxime derivative of the Formula V or an acid addition salt thereof in the presence of a base, and using by the ring-closure of the oxime of the Formula II formed a $C_{1-4}$-alkanol as inert solvent.

It has been found that risperidone can be economically prepared with high yields in pure form by subjecting the oxime of the Formula II to cyclization in the presence of an alkali hydroxide, alkali carbonate or alkali-$C_{1-4}$-alkoxide in an inert organic solvent, converting the base of the Formula I thus formed into an acid addition salt or setting free the base of the Formula I from an acid addition salt thereof, whereby a halogen derivative of the general Formula XIV (wherein Hal is halogen) is reacted with the piperidone oxime derivative of the Formula V or an acid addition salt thereof in the presence of a base and by the ring-closure of the oxime of the Formula II thus formed a $C_{1-4}$-alkanol is used as inert solvent.

By the preparation of the oxime of the Formula II as base an inorganic base (e.g. sodium hydrogencarbonate or potassium carbonate) or an organic base (e.g. triethylamine or pyridine) can be used.

According to the process of the present invention after the reaction of the halogen derivative of the general Formula XIV and the piperidine oxime derivative of the Formula V or an acid addition salt thereof the oxime of the Formula II precipitates in crystalline form and can be converted in the presence of a $C_{1-4}$-alkanol into risperidone of the Formula I with a yield of about 95%.

The process of the present invention is surprising for the person skilled in the art because it could not be foreseen that the piperidine oxime derivative of the Formula V containing two acidic hydrogen atoms or a salt thereof would be alkylated in the presence of a base selectively only on the nitrogen atom. This is so much the more surprising as the oxime of the Formula II can be isolated with a yield exceeding 80%.

It is furthermore also surprising that while according to ES-P 2,050,069 the ring-closure of the oxime of the Formula II is carried out with a yield of about 75% only, the process of the present invention enables the carrying out the cyclization with a yield of about 95%.

The advantage of the process of the present invention is that a pharmaceutically pure product can be prepared in high yields.

Further details of the present invention are to be found in the following Examples without limiting the scope of protection to said Examples.

EXAMPLE 1

Preparation of 3-[2-[4-[(2,4-difluorophenyl)-(hydroxyimino)-methyl]-1-piperidinyl]ethyl]-6,7,8,9-tetrahydro-2-methyl-4H-pyrido[1,2-a]pyrimidin-4-one (compound of the Formula II)

To a solution of 36.0 g (0.16 mole) of 3-(2-chloroethyl)-6,7,8,9-tetrahydro-2-methyl-4H-pyrido[1,2-a]pyrimidin-4-one in 800 ml of acetonitrile 44.3 g of 4-(2,4-difluorobenzoyl)-piperidine-oxime-hydrochloride, 33.6 g of sodium hydrogen carbonate and 0.66 g (4 millimoles) of potassium iodide are added. The reaction mixture is refluxed for 5 hours, cooled to room temperature and the solvent is removed in vacuo. The residue is taken up in 700 ml of water and extracted twice with 600 ml of dichloromethane each. The combined organic layers are dried over sodium sulfate and evaporated in vacuo. Thus 63.7 g of the title compound are obtained. Yield 92.5%. M.p.: 180-183° C.

EXAMPLE 2

Preparation of 3-[2-[4-[(2,4-difluorophenyl)-(hydroxyimino)-methyl]-1-piperidinyl]ethyl]-6,7,8,9-tetrahydro-2-methyl-4H-pyrido[1,2-a]pyrimidin-4-one (compound of the Formula II)

One proceeds as described in Example 1 except that methanol is used in place of acetonitrile. Thus 60.7 g of a product being identical in all respects with the compound prepared according to Example 1 are obtained. Yield 88.2%.

EXAMPLE 3

Preparation of 3-[2-[4-[(2,4-difluorophenyl)-(hydroxyimino)-methyl]-1-piperidinyl]ethyl]-6,7,8,9-tetrahydro-2-methyl-4H-pyrido[1,2-a]pyrimidin-4-one (compound of the Formula II)

One proceeds as described in Example 1 except that ethanol is used in place of acetonitrile. Thus 62.1 g of a product being identical in all respects with the compound prepared according to Example 1 are obtained. Yield 90.1%.

EXAMPLE 4

Preparation of 3-{2-[4-(6-fluoro-1,2-benzisoxazol-3-yl)-1-piperidinyl]ethyl}-6,7,8,9-tetrahydro-2-methyl-4H-pyrido[1,2-a]pyrimidin-4-one (risperidone of the Formula I)

To a solution of 5.4 g (0.1 mole) of sodium methylate in 60 ml of methanol 8.6 g (0.02 mole) of 3-[2-[4-[(2,4-difluorophenyl)-(hydroxyimino)-methyl]-1-piperidinyl]ethyl]-6,7,8,9-tetrahydro-2-methyl-4H-pyrido[1,2-a]pyrimidin-4-one are added with stirring at room temperature. The reaction mixture is refluxed for half an hour, then 100 ml of water are added. The precipitated crystalline product is filtered off, washed with water and dried. Thus 7.9 g of the title compound are obtained. Yield 96.3%. According to HPLC analysis the total amount of the impurities is below 0.2% and the product contains no contamination in an amount above 0.1% each. The product meets the requirements of Pharmeuropa Vol. 10, No. 2, June 1988 in all respects.

EXAMPLE 5

Preparation of 3-{2-[4-(6-fluoro-1,2-benzisoxazol-3-yl)-1-piperidinyl]ethyl}-6,7,8,9-tetrahydro-2-methyl-4H-pyrido[1,2-a]pyrimidin-4-one (risperidone of the Formula I)

One proceeds as described in Example 4 except that ethanol is used in place of methanol. Thus 7.7 g of the title compound are obtained. Yield 94.5%. The product is identical in all respects with the compound prepared according to Example 4.

EXAMPLE 6

Preparation of 3-{2-[4-(6-fluoro-1,2-benzisoxazol-3-yl)-1-piperidinyl]ethyl}-6,7,8,9-tetrahydro-2-methyl-4H-pyrido[1,2-a]pyrimidin-4-one (risperidone of the Formula I)

One proceeds as described in Example 4 except that 2-propanol is used in place of methanol. Thus 7.5 g of the title compound are obtained. Yield 91.4%. The product is identical in all respects with the compound prepared according to Example 4.

COMPARATIVE EXAMPLE 1

Preparation of 4-(6-fluoro-1,2-benzisoxazol-3-yl)-piperidine (compound of the Formula IV; reproduction of Example 1 Paragraph 4 of HU-P 195,793)

A suspension of 11 g of 4-(2,4-difluoro-benzoyl)piperidine-oxime hydrochloride and 25 g of potassium hydroxide in 25 ml of water is heated to boiling with stirring for 2 hours. The reaction mixture is cooled to room temperature and extracted with toluene. The organic phase is dried over anhydrous sodium sulfate and evaporated in vacuo. The residual crude product is recrystallized from petroleum ether. Thus 7.1 g of the title compound are obtained. According to HPLC MS analysis the product contains 5% of 4-{6-[4'-(6'-fluoro-1',2'-benzisoxazol-3'-yl)-piperidine-1'-yl]-1,2-benzisoxazol-3-yl}-piperidine, as a contamination (compound of the Formula VI).

2.0 g of the above product is subjected to separation by column chromatography (eluent:chloroform-methanol 9:1). Thus 57 mg of 4-{6-[4'-(6'-fluoro-1',2'-benzisoxazol-3'-yl)-piperidine-1'-yl]-1,2-benzisoxazol-3-yl}-piperidine are obtained. M.p.: 234-237° C.

pmr (DMSO-$d_6$): δ, ppm 1.95(m, 4H, piperidine-$CH_2$-3',5'), 2.12(m, 4H, piperidine-3,5), 3.10(m, 4H, piperidine-$NCH_2$-2,6), 3.34(b, xH, piperidine-$NCH_2$-2',6'+water), 4.03 (m, 2H, piperidine-4+piperidine-4'), 7.13(m, 2H, phenyl-4,5), 7.31(m, 1H, phenyl-5'), 7.68-7.80(m, 2H, phenyl-7+phenyl-7'), 8.05(m, 1H, phenyl-4').

COMPARATIVE EXAMPLE 2

A) Preparation of 3-{2-[4-(6-fluoro-1,2-benzisoxazol-3-yl)-1-piperidinyl]ethyl}-6,7,8,9-tetrahydro-2-methyl-4H-pyrido[1,2a]pyrimidin-4-one (risperidone of the Formula I; reproduction of Example 1 Paragraph 5 of HU-P 195,793)

A mixture of 5.3 g (0.02 mole) of 3-(2-chloroethyl)-6,7,8,9-tetrahydro-2-methyl-4H-pyrido[1,2-a]pyrimidin-4-one, 4.4 g (0.02 mole) of 4-(6-fluoro-1,2-benzisoxazol-3-yl)-piperidine, 8 g (0.075 mole) of sodium carbonate and 0.1 g of potassium iodide in 90 ml of N,N-dimethylformamide is heated at 85-90° C. with stirring overnight. The reaction mixture is cooled, poured into water and the precipitated crystalline product is recrystallized from a mixture of N,N-dimethyl formamide and 2-propanol. Thus 3.6 g of the title compound are obtained. Yield 45%. M.p.: 168-170° C. According to HPLC-MS analysis the product contains 3% of 3-{2-[4-{6-(6'-fluoro-1',2'-benzisoxazol-3'-yl)-1'-piperidinyl]-1,2-benzisoxazol-3-yl}-1-piperidinyl]ethyl}-6,7,8,9-tetrahydro-2-methyl-4H-pyrido[1,2-a]pyrimidin-4-one as contaminant compound of the Formula VII.

2.5 g of the above product are subjected to separation by column chromatography (eluent: chloroform-methanol 9:1). Thus 10 mg of pure 3-{2-[4-{6-(6'-fluoro-1',2'-benzisoxazol-3'-yl)-1'-piperidinyl]-1,2-benzisoxazol-3-yl}-1-piperidinyl]ethyl}-6,7,8,9-tetrahydro-2-methyl-4H-pyrido[1,2-a]pyrimidin-4-one contamination are obtained. M.p.: 208-213° C.

B) Preparation of 3-{2-[4-{6-(6'-fluoro-1',2'-benzisoxazol-3'-yl)-1'-piperidinyl]-1,2-benzisoxazol-3-yl}-1-piperidinyl]ethyl}-6,7,8,9-tetrahydro-2-methyl-4H-pyrido[1,2-a]pyrimidin-4-one (compound of the Formula VII)

A solution of 50 mg (0.12 millimole) of 4-{6-[4'-(6'-fluoro-1',2'-benzisoxazol-3'-yl)-piperidine-1'-yl]-1,2-benzisoxazol-3-yl}-piperidine prepared according to comparative Example 1, 27 mg (0,12 millimole) of 3-(2-chloroethyl)-6,7,8,9-tetrahydro-2-methyl-4H-pyrido[1,2-a]pyrimidin-4-one, 82 mg (0.6 millimole) of potassium carbonate and a catalytic amount of potassium iodide in acetonitrile is heated to boiling with stirring for 6 hours. The reaction mixture is cooled and the solvent is evaporated in vacuo. To the residue 5 ml of water are added and the mixture is extracted twice with 5 ml of dichloromethane each. The organic phase is dried over anhydrous sodium sulfate and evaporated in vacuo. Thus 50 mg of the title compound are obtained. Yield 68%. M.p.: 209-213° C. The product is identical in all respects with the product isolated by chromatography according to paragraph A). pmr (DMSO-$d_6$): δ, ppm 1.8(m, 6H, tetrahydro-pyrido[1,2-α]pyrimidin-7,8,9), 2.10(m, 4H, piperidine-$CH_2$-3',5'), 2.12 (m, 4H, piperidine-3,5), 2.30(s, 3H, $CH_3$), 2.55(t, 2H, $CH_2$), 2.83(t, 2H, $CH_2$), 3.18(m, 4H, piperidine-$NCH_2$-2,6), 3.30 (b, xH, piperidine-$NCH_2$-2',6'), 4.01(m, 2H, piperidine-4+ piperidine-4'), 7.11(m, 2H, phenyl-4,5), 7.30(m, 1H, phenyl-5'), 7.61-7.83(m, 2H, phenyl-7+phenyl-7'), 8.00(m, 1H, phenyl-4').

COMPARATIVE EXAMPLE 3

Reproduction of Examples 8, 9, 10 and 11 of ES-P 2,050,069

A) Preparation of 3-[2-[4-(2,4-difluoro-benzoyl)-piperidino]ethyl]-6,7,8,9-tetrahydro-2-methyl-4H-pyrido[1,2-a]pyrimidin-4-one A suspension of 29.2 g (0.1116 mole) of 4-(2,4-difluoro-benzoyl)-piperidine-hydrochloride, 25.3 g (0.1117 mole) of 3-(2-chloroethyl)-6,7,8,9-tetrahydro-2-methyl-4H-pyrido[1,2-a]pyrimidin-4-one, 500 ml of acetonitrile, 19.6 g (0.2333 mole) of sodium hydrogencarbonate and 0.25 g (0.0015 mole) of potassium iodide is heated to boiling for 10 hours with stirring. The reaction mixture is cooled to room temperature, to the residue 200 ml of water are added. The mixture is stirred for 30 minutes and extracted with 200 ml of dichloromethane. The organic phase is separated, dried over magnesium sulfate, filtered and the filtrate is evaporated. The oily residue thus obtained is purified as follows:

I) The oily residue is purified on a silica column; eluent: chloroform-methanol 9:1. The fractions containing the product are collected and evaporated. The residue is dissolved in 200 ml of dichloromethane, the solution is saturated with gaseous hydrogen chloride. The precipitated crystalline product is filtered and dried. Thus 32.1 g of the title compound are obtained. Yield 58.9%. According to HPLC chromatography the purity of the product is 96.8%.

II) The oily residue is dissolved in 200 ml of dichloromethane, the solution is saturated with gaseous hydrogen chloride. Because no crystalline product is precipitated from the solution, the solvent is evaporated.

The residual oily product is triturated with diethyl ether for a longer period of time. Crystallization is initiated by seeding with a crystal of the desired compound. Thus 27.9 g of the title compound are obtained. Yield 51.2%. According to HPLC analysis the purity of the product is 94.8%.

B) Preparation of 3-[2-[4-[(2,4-difluorophenyl)-(hydroxyimino)-methyl]-1-piperidinyl]ethyl]-6,7,8,9-tetrahydro-2-methyl-4H-pyrido[1,2-a]pyrimidin-4-one To a solution of 7.0 g (0.0143 mole) of 3-[2-[4-(2,4-difluoro-benzoyl)-piperidino]ethyl]-6,7,8,9-tetrahydro-2-methyl-4H-pyrido[1,2-a]pyrimidin-4-one, 70 ml of pyridine, 5.4 g (0.0777 mole) of hydroxylamine hydrochloride and 100 ml of ethanol 1.6 g (0.0286 mole) of potassium hydroxide are added. The reaction mixture is heated to boiling for 10 hours, cooled to room temperature and the solvent is removed in vacuo. To the residue 100 ml of water are added and the mixture is extracted with 100 ml of dichloromethane. The organic phase is washed twice with 50 ml of water each, dried over anhydrous magnesium sulfate and evaporated. The residual crude product is recrystallized from ethyl acetate. Thus 4.2 g of 3-[2-[4-[(2,4-difluorophenyl)-(hydroxyimino)-methyl]-1-piperidinyl]ethyl]-6,7,8,9-tetrahydro-2-methyl-4H-pyrido[1,2-a]pyrimidin-4-one are obtained. Yield 65.1%. According to HPLC analysis the purity of the product is 97.2%.

C) Preparation of 3-{2-[4-(6-fluoro-1,2-benzisoxazol-3-yl)-1-piperidinyl]ethyl}-6,7,8,9-tetrahydro-2-methyl-4H-pyrido[1,2-a]pyrimidin-4-one To a suspension of 40 mg (0.9166 millimole) of 55% sodium hydride and 2 ml of tetrahydrofurane 0.1089 g (0.2532 millimole) of 3-[2-[4-[(2,4-difluorophenyl)-(hydroxyimino)-methyl]-1-piperidinyl]ethyl]-6,7,8,9-tetrahydro-2-methyl-4H-pyrido[1,2-a]pyrimidin-4-one is added. The reaction mixture is heated to boiling for an hour, whereupon 5 ml of water are added and the mixture is extracted twice with 10 ml of dichloromethane each. The combined organic phases are dried over magnesium sulfate and evaporated in vacuo. Thus 80 mg of the title compound are obtained, yield 77%. According to HPLC analysis the purity of the product is 97.5%.

D) Preparation of 3-{2-[4-(6-fluoro-1,2-benzisoxazol-3-yl)-1-piperidinyl]ethyl}-6,7,8,9-tetrahydro-2-methyl-4H-pyrido[1,2-a]pyrimidin-4-one A solution of 1 g (0.0023 mole) of 3-[2-[4-[(2,4-difluorophenyl)-(hydroxyimino)-methyl]-1-piperidinyl]ethyl]-6,7,8,9-tetrahydro-2-methyl-4H-pyrido[1,2-a]pyrimidin-4-one and 1 g of potassium hydroxide in 10 ml of water is heated to boiling for an hour. The reaction mixture is cooled to room temperature and extracted twice with 10 ml of dichloromethane each. The organic phase is evaporated. Thus 0.70 g of 3-{2-[4-(6-fluoro-1,2-benzisoxazol-3-yl)-1-piperidinyl]ethyl}-6,7,8,9-tetrahydro-2-methyl-4H-pyrido[1,2-a]pyrimid-in-4-one are obtained, yield 73.5%. According to HPLC analysis the purity of the product is 96.4%.

We claim:

1. Process for the preparation of 3-{2-[4-(6-fluoro-1,2-benzisoxazol-3-yl)-1-piperidinyl]ethyl}-6,7,8,9-tetrahydro-2-methyl-4H-pyrido[1,2-a]pyrimidin-4-one of the Formula

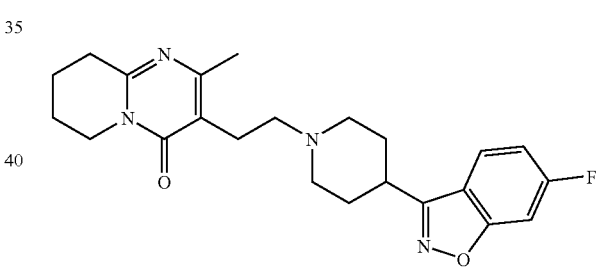

I and pharmaceutically acceptable acid addition salts thereof by subjecting the oxime of the Formula

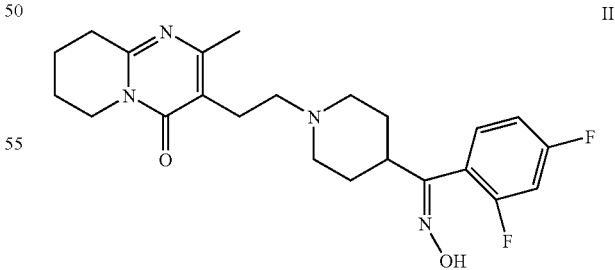

II to ring-closure in the presence of an alkali hydroxide, alkali carbonate or alkali-$C_{1-4}$-alkoxide in an inert organic solvent, converting the base of the Formula I thus obtained into an acid addition salt or setting free the base of the Formula I from an acid addition salt thereof which comprises reacting a halogen derivative of the general Formula

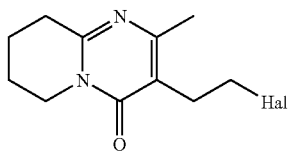

(wherein Hal is halogen) with piperidine oxime derivative of the Formula

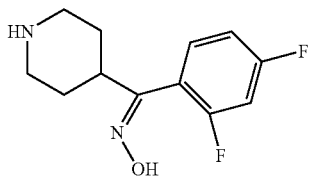

or an acid addition salt thereof in the presence of a base, and using by the ring-closure of the oxime of the Formula II formed a $C_{1-4}$-alkanol as inert solvent.

2. Process according to claim 1 which comprises using a halogen derivative of the general Formula XIV wherein Hal stands for chlorine.

3. Process according to claim 1 which comprises using the hydrochloride salt of the piperidine oxime derivative of the Formula V.

4. Process according to claim 1 which comprises using sodium hydrogencarbonate as base.

5. Process according to claim 1 which comprises using methanol as $C_{1-4}$-alkanol.

6. Process according to claim 1 which comprises using ethanol as $C_{1-4}$-alkanol.

7. Process according to claim 1 which comprises using isopropanol as $C_{1-4}$-alkanol.

* * * * *